United States Patent [19]

Mobilio et al.

[11] Patent Number: 4,782,076

[45] Date of Patent: Nov. 1, 1988

[54] SUBSTITUTED 2,3,4,9-TETRAHYDRO-1H-CARBAZOLE-1-ACETIC ACID DERIVATIVES, COMPOSITION AND USE

[75] Inventors: Dominick Mobilio, Franklin Park; Leslie G. Humber, North Brunswick, both of N.J.

[73] Assignee: American Home Products Corporation, New York, N.Y.

[21] Appl. No.: 162,443

[22] Filed: Mar. 1, 1988

[51] Int. Cl.$^4$ .................. A61K 31/40; C07D 209/86
[52] U.S. Cl. .................................. 514/411; 548/439
[58] Field of Search ...................... 548/439; 514/411

[56] References Cited

U.S. PATENT DOCUMENTS 4,578,398  3/1986  Mobilio et al. ...................... 548/439
4,584,312  4/1986  Mobilio et al. ...................... 548/439
4,616,028 10/1986  Mobilio et al. ...................... 548/439

*Primary Examiner*—Robert W. Ramsuer
*Attorney, Agent, or Firm*—Walter Patton

[57] ABSTRACT

Substituted 2,3,4,9-tetrahydro-1H-carbazole-1-acetic acid derivatives and methods of their preparation and use are disclosed. The compounds are useful analgesic and anti-inflammatory agents.

7 Claims, No Drawings

SUBSTITUTED 2,3,4,9-TETRAHYDRO-1H-CARBAZOLE-1-ACETIC ACID DERIVATIVES, COMPOSITION AND USE

BACKGROUND OF THE INVENTION a. Field of Invention

This invention relates to tricyclic acetic acid derivatives, to their preparation and use, and to intermediates used for their preparation.

More specifically, this invention relates to tricyclic acetic acid derivatives in which the tricyclic portion thereof is characterized by having an indole portion fused to a cyclohexane ring. Still more specifically, the compounds of this invention are characterized as derivatives of the following tricyclic acetic acid system:

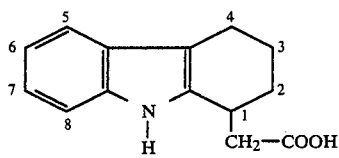

2,3,4,9-tetrahydro-1H-carbazole-1-acetic acid in which the carbons at the 1-, 4-, 5-, 6-, 7- and 8- positions are further substituted.

The tricyclic acetic acid compounds of this invention possess useful pharmacologic properties; for instance, they exhibit analgesic and anti-inflammatory activity at dose levels which do not elicit undesirable side effects. The foregoing combination of attributes renders the compounds of this invention useful for the treatment of inflammatory or painful conditions in a mammal.

b. Prior Art

The closest prior art to the present invention is: U.S. Pat. Nos. 4,616,028; 4,584,312 and 4,578,398.

Demerson et al, U.S. Pat. No. 3,939,178 discloses 1,3,4,9-tetrahydropyrano[3,4-b]indoles and 1,3,4,9-tetrahydrothiopyrano[3,4-b]indoles having analgesic and anti-inflammatory activity.

Boehringer Mannheim European Pat. No. 42593 generically discloses starting materials useful for producing cardiotonic and beta-blocking agents. The starting materials include 1,2,3,4-tetrahydrocarbazoles with substituents selected from the broad group including hydrogen, carboxy, lower alkyl and lower alkenyl. The starting materials are in each case also substituted with a reactive group which distinguishes them from the compounds of the present invention.

SUMMARY OF THE INVENTION

The compounds of this invention are represented by formula (I)

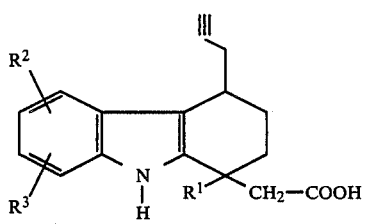

wherein $R^1$ is hydrogen or lower alkyl containing 1 to 6 carbon atoms and $R^2$ and $R^3$ are independently hydrogen, halogen or lower alkyl containing 1 to 6 carbon atoms and the pharmaceutically acceptable salts thereof.

A preferred aspect of this invention is represented by formula (II)

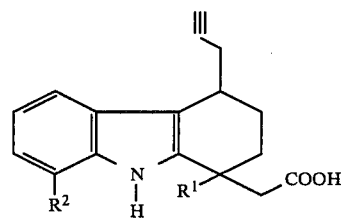

wherein $R^1$ is hydrogen or lower alkyl containing 1 to 6 carbon atoms; $R^2$ is hydrogen, halogen or lower alkyl containing 1 to 6 carbon atoms and the pharmaceutically acceptable salts thereof.

A still further preferred aspect of the present invention are the compounds represented by formula (II), wherein $R^1$ and $R^2$ are lower alkyl containing 1 to 6 carbon atoms and the pharmaceutically acceptable salts thereof.

A still further preferred aspect of the present invention are the compounds represented by formula (II), wherein $R^1$ and $R^2$ are ethyl and the pharmaceutically acceptable salts thereof.

The most preferred compound of the present invention is designated 1,8-diethyl-2,3,4,9-tetrahydro-4-(2-propynyl)-1H-carbazole-1-acetic acid isomer A and the pharmaceutically acceptable salts thereof.

The compounds of the present invention are prepared by a process in which the unsaturated ketone of structure (III),

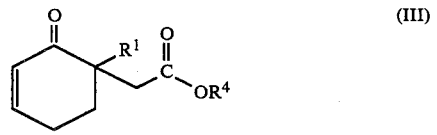

prepared as described by Mobilio et al, in U.S. Pat. No. 4,578,398, wherein $R^1$ is hydrogen or lower alkyl containing 1 to 6 carbon atoms and $R^4$ is lower alkyl containing 1 to 6 carbon atoms, is reduced to diol (IV)

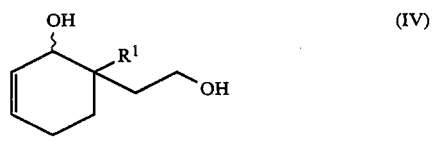

with a metal or hydride reducing agent. A preferred method is to reduce (III) to (IV) with lithium aluminum hydride in ether.

The primary alcohol group in (IV) is then protected with a suitable alcohol protecting group such as

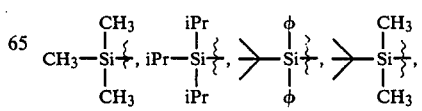

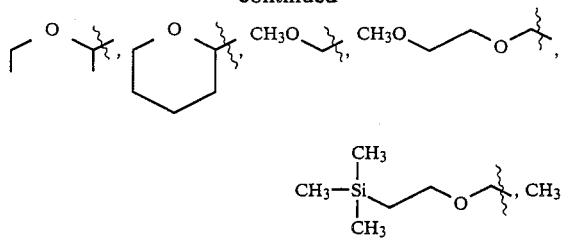

or other ether or acetal protecting group to afford a compound of formula (V)

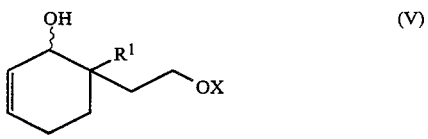

wherein X is the protecting group. The preferred protecting group is when X is tert-butyldiphenylsilyl

which can be prepared by treating (IV) with tert-butyldiphenylsilylchloride in the presence of a base. The free alcohol in (V) is then oxidized to the enone (VI)

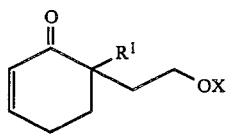

wherein R¹ and X are as defined above with a suitable oxidizing agent such manganese dioxide or pyridinium chlorochromate. A preferred method is to oxidize (V) with pyridinium dichromate in methylene chloride. Enone (VI) is then treated with the lithium reagent (VII)

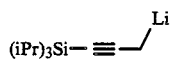

in a tetrahydrofuran/hexamethylphosphoramide solvent mixture below 0° C., preferably at −78° C., affording ketone (VIII)

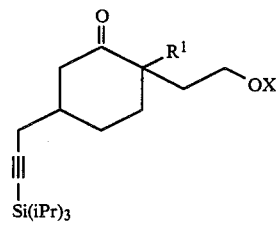

wherein R¹ and X are as defined above.

The protecting group X and the tri-isopropylsilyl group are then removed either by removing X then (iPr)₃Si, or by removing (iPr)₃Si then X. When X is a silyl protecting group, such as

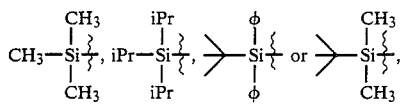

and preferrably tert-butyldiphenylsilyl, removal of both X and the silyl protecting group can be accomplished simultaneously by treatment with fluoride ion. This is preferably done with tetrabutylammonium fluoride in tetrahydrofuran to provide one or two products having R/s of approximately 0.2 and 0.73 (15% ethyl acetate in petroleum ether, silica gel). Either of the products alone or both together can then be oxidized with a suitable oxidizing agent to the same carboxylic acid and then esterified by treatment with diazomethane or an alcohol in the presence of an acid to afford ketone (IX)

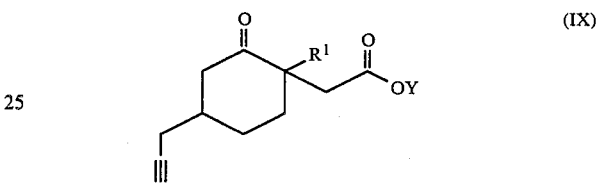

wherein R¹ is as defined above and Y is hydrogen or lower alkyl containing 1 to 6 carbon atoms. The oxidation is preferably done by oxidizing with Jones' reagent in acetone (L. F. Fieser and M. Fieser, "Reagents for Organic Synthesis," John Wiley and Sons, Inc., New York, 1967, pages 142–144) followed by treatment of the acid with diazomethane. Ketone (IX) is then condensed with a substituted hydrazine of formula (X)

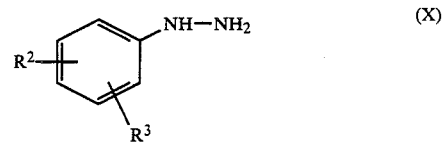

wherein R² and R³ are as defined above to obtain the corresponding hydrazone of formula (XI)

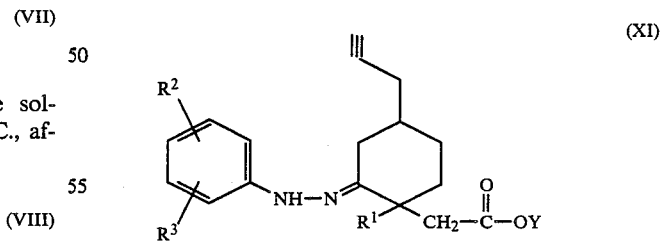

wherein R¹, R², R³ and Y are as defined above. The hydrazone is treated with a cyclizing agent to give the ester of compound (I) designated (XII) which is a useful intermediate in the preparation of compound (I), and after hydrolyzing said ester compound (I) is obtained.

Generally speaking, the condensation of (IX) and (X) is performed preferably in an inert atmosphere, for example, nitrogen or argon. Suitable solvents for the condensatin include the lower alkanols such as methanol and ethanol; aromatics such as benzene and toluene;

the ethers, such as tetrahydrofuran, diethyl ether, dioxane, bis(2-methoxyethyl)-ether and the like; and the halogenated hydrocarbons, methylene chloride, chloroform and the like. Methanol and ethanol are especially convenient and practical solvents. Times and temperatures for the condensation generally range from 5 minutes to five or six days at 0° to 100° C. Convenient time and temperature ranges include 20° C. to the boiling point of the mixture and 15 minutes to 130 hours.

The resulting hydrazones (XI) are then cyclized to the tricyclic ester of the acid of formula (I) by the action of a suitable cyclization agent according to the conditions of the "Fischer Indole Synthesis," for example, see B. Robinson, Chem. Rev. 63, 373 (1963).

A variety of cyclization agents are effective for this cyclization, some of the agents suitable for this cyclization include p-toluenesulfonic acid, hydrogen chloride or hydrogen chloride generated from acetyl chloride, hydrogen bromide, phosphoric acid, sulfuric acid, aluminum chloride, zinc chloride, hydrogen bromide in acetic acid, boron trifluoride-etherate, trifluoroacetic acid, cationic ion exchange resins such as Amberlite IR-120, phenyl or ethyl magnesium bromide and aniline salts. In other words the usual catalysts employed for the "Fischer Indole Synthesis" are efficacious; however, the preferred cyclization agents are hydrogen chloride or hydrogen chloride generated from acetyl chloride.

In practice the isolation of the hydrazone (XI) from the condensation reaction mixture is optional. Accordingly, the cyclization agent is added either to the above condensation reaction mixture containing the hydrazone, or to the isolated hydrazone optionally dissolved in one of the above solvents, whereby the hydrazone then cyclizes to give the corresponding tricyclic ester of formula (I) in which $R^1$ to $R^3$ inclusive are as defined hereinbefore.

The cyclization usually proceeds smoothly and rapidly. Convenient reaction times for the cyclization include five minutes to two hours, preferably 30 minutes to one hour. Convenient temperatures include 20° to 200° C., preferably 120° to 180° C.

In practice a most convenient and practical procedure for effecting the above cyclization comprises evaporating solvent from the condensation reaction mixture containing the hydrazone, and then heating the hydrazone at 120° to 200° C. in one of the aformentioned solutions of strong acids.

In producing the material of formula (IX) the esterification step may be left out, so (IX) may be either a cycloalkanoneacetic acid derivative or its corresponding lower alkyl ester (Y=lower alkyl). Accordingly, when the acid is employed, the above process yields the tricyclic compound identical to the desired compound of formula (I) and when the starting material is lower alkyl ester the above process yields the lower alkyl ester tricyclic compound of formula (I).

The subsequent conversion of the lower alkyl ester tricyclic compound of formula (I) to the corresponding compound of formula (I) is effected readily by subjecting the tricyclic compound to hydrolysis. Generally speaking, this conversion is most conveniently performed by employing a base as the hydrolyzing agent. The hydrolysis is performed in the presence of sufficient water optionally under an inert atmosphere, followed by acidification of the reaction mixture to yield the desired compound of formula (I). However, the manner of hydrolysis is not intended to be limited to basic hydrolysis since hydrolysis under acidic conditions and other variations, for example, treatment with lithium iodide in collidine (see L. F. Fieser and M. Fieser, "Reagents for Organic Synthesis," John Wiley and Sons, Inc., New York, 1967, pp. 615–617) are also applicable.

For basic hydrolysis a preferred embodiment involves subjecting the tricyclic ester to the action of a base, for example, sodium or potassium carbonate, in the presence of sufficient water to effect hydrolysis of the ester. The hydrolysis is performed using a suitable solvent, for example, methanol or ethanol under a nitrogen atmosphere.

The reaction mixture is maintained at a temperature of from 25° C. to the reflux temperature until hydrolysis occurs. Usually from 10 minutes to 48 hours is sufficient for this hydrolysis. The reaction mixture is then rendered acidic with an acid, for example, acetic acid, hydrochloric acid, sulfuric acid and the like, to release the free acid as a solid.

Alternatively, the tricyclic ester is hydrolyzed by subjecting the ester to the action of a hydrolyzing agent which is a strong organic or inorganic acid, for example, trifluoroacetic acid, p-toluenesulfonic acid, hydrochloric acid, hydrobromic acid, hydroiodic acid, sulfuric acid, phosphoric acid and the like in a suitable solvent at a temperature of at least 60° C. and preferably from 90° C. to the boiling point of the mixture until the hydrolysis occurs. Usually from 5 to 48 hours are required for this hydrolysis. Suitable solvents include water, acetic acid, aqueous alcohols and the like. If acid hydrolysis is used, the free acid is formed directly. If necessary, the reaction mixture can be diluted with water to precipitate the product.

DETAILED DESCRIPTION OF THE INVENTION

The term "lower alkyl" as used herein contemplates straight chain alkyl radicals containing from one to six carbon atoms and branched chain alkyl radicals containing from three to four carbon atoms and includes methyl, ethyl, propyl, isopropyl, butyl, isobutyl, pentyl, hexyl and the like.

The term "halogen" as used herein includes fluorine, chlorine, bromine and iodine.

The compounds of formula (I) form salts with suitable pharmaceutically acceptable inorganic and organic bases. These derived salts possess the same activity as the parent acid and are included within the scope of this invention. The acid of formula (I) is transformed in excellent yield into the corresponding pharmaceutically acceptable salts by neutralization of said acid with the appropriate inorganic or organic base. The salts are administered in the same manner as the parent acid compounds. Suitable inorganic bases to form these salts include, for example, the hydroxides, carbonates, bicarbonates or alkoxides of the alkali metals or alkaline earth metals, for example, sodium, potassium, magnesium, calcium and the like. Suitable organic bases include the following amines; lower mono-, di- and trialkylamines, the alkyl radicals of which contain up to three carbon atoms, such as methylamine, dimethylamine, trimethylamine, ethylamine, di- and triethylamine, methylethylamine, and the like; mono, di- and trialkanolamines, the alkanol radicals of which contain up to three carbon atoms, such as mono-, di- and triethanolamine; alkylenediamines which contain up to six carbon atoms, such as hexamethylenediamine; amino sugars, such as glucosamine; phenyl substituted alkylamines, such as benzenemethanamine or N,N-bis-(phenylmethyl)-1,2-ethanediamine; cyclic saturated or unsaturated bases containing up to six carbon atoms, such as pyrrolidine, piperidine, morpholine, piperazine and their N-alkyl and N-hydroxyalkyl derivatives, such as N-methylmorpholine and N-(2-hydroxyethyl)piperidine, as well as pyridine. Furthermore, there may be mentioned the corresponding quaternary salts, such as the tetraalkyl (for example tetramethyl), alkyl-alkanol (for example methyltrimethanol and trimethyl-monoethanol) and cyclic ammonium salts, for example the N-methyl-pyridinium, N-methyl-N-(2-hydroxyethyl)-morpholinium, N,N-dimethyl-morpholinium, N-methyl-N-(2-hydroxyethyl)-morpholinium, N,N-dimethyl-piperidinium salts, which are characterized by good water-solubility. In principle, however, there can be used all the ammonium salts which are physiologically compatible.

The transformations to the salts can be carried out by a variety of methods known in the art. For example, in the case of the inorganic salts, it is preferred to dissolve the acid of formula (I) in water containing at least one equivalent amount of a hydroxide, carbonate, or bicarbonate corresponding to the inorganic salt desired. Advantageously, the reaction is performed in a water-miscible organic solvent inert to the reaction conditions, for example, methanol, ethanol, dioxane, and the like in the presence of water. For example, such use of sodium hydroxide, sodium carbonate or sodium bicarbonate gives a solution of the sodium salt. Evaporation of the solution or addition of a water-miscible solvent of a more moderate polarity, for example, a lower alkanol, for instance, butanol, or a lower alkanone, for instance, ethyl methyl ketone, gives the solid inorganic salt if that form is desired.

To produce an amine salt, the acid of formula (I) is dissolved in a suitable solvent of either moderate or low polarity, for example, ethanol, acetone, ethyl acetate, diethyl ether and benzene. At least an equivalent amount of the amine corresponding to the desired cation is then added to that solution. If the resulting salt does not precipitate, it can usually be obtained in solid form by addition of a miscible diluent of low polarity, for example, benzene or petroleum ether, or by evaporation. If the amine is relatively volatile, any excess can easily be removed by evaporation. It is preferred to use substantially equivalent amounts of the less volatile amines.

Salts wherein the cation is quaternary ammonium are produced by mixing the acid of formula (I) with an equivalent amount of the corresponding quaternary ammonium hydroxide in water solution, followed by evaporation of the water.

Included in the present invention are the diastereoisomers wherein the 4-substituent is either cis or trans to the acetic acid chain at position one.

Also included in this invention are the optical isomers of the compounds of formula (I) which result from asymmetric centers, contained therein. Such isomers are obtained in substantially pure form by classical separation techniques and by sterically controlled synthesis.

Anti-inflammatory Activity

The useful anti-inflammatory activities of the tricyclic acetic acid derivatives of formula (I) are demonstrated in standard pharmacologic tests, for example, the test designated: PREVENTIVE ADJUVANT EDEMA The objective of this test is to determine the ability of test drugs to exhibit an acute anti-inflammatory effect in rats. This test is a primary screen for anti-inflammatory drugs.

Species:

Male Sprague Dawley rats (180–200 g) are used. The animals have free access to water but food is withdrawn 18 hours before testing.

Drug Preparations and Administration:

Freund's complete adjuvant is prepared by suspending 5 mg killed and dried *Mycobacterium butyricum* (Difco) in 1 mL liquid paraffin. The test compounds are dissolved in distilled water or suspended in 0.5% Tween 80 in distilled water according to their solubility. For primary screening all drugs are administered by gastric lavage at the arbitrary dosage of 25 mg/kg, p.o. in a volume of 0.5 mL/100 g body weight to groups of 10 animals.

Methodological Details:

The method is essentially that described by Wax et al, J. Pharmacol. Exp. Ther., 192, 166–171 (1975). Groups of rats are injected intradermally in the left hind paw with 0.1 mL of Freund's complete adjuvant. The test compound or vehicle is administered immediately before the adjuvant, 24 hours and 48 hours after the adjuvant (day 0, 1 and 2). The injected hind paw volume is measured before the injection of adjuvant and 24 hours after the last drug administration (day 3) by means of a plethysmometer (Buxco Electronics Inc.). The difference between the hind paw volume on day 0 and day 3 represents the edema volume. Etodolac (25 mg/kg, p.o.) is included as a positive control.

Presentation of Results:

The mean edema volume (expressed in mL±SEM) is calculated for each group and the percentage inhibition of inflammation conferred by the drug is calculated:

$$\% \text{ inhibition} = \left[ \frac{c - t}{c} \right] \times 100$$

where c is the mean edema volume for the untreated controls and t is the means edema volume for the drug treated group.

A further test used to determine the utility of the compounds of the present invention is designated: DRUG EFFECTS ON PHENYLBENZOQUINONE-INDUCED WRITHING IN MICE The objective of this test is to determine the ability of test drugs to inhibit the nociceptive (pain) response of mice injected with a chemical irritant. This test is a primary screen for both peripheral and centrally acting analgesic drugs.

Species:

Male Swiss albino mice (15–25 g) are used. The animals are fasted for 18 hours prior to use but have free access to water.

Drug Preparation and Administration:

Drugs are dissolved or suspended according to their solubility in 0.5% Tween 80 in distilled water. They are administered by gastric lavage in a volume of 5 mL/kg. For primary screening all drugs are administered at the arbitary dosage of 25 mg/kg, p.o. to a group of 10 mice.

Methodological Details:

A modification of the method of Siegmund et al, Proc. Soc. Exp. Biol. Med., 95, 729–731 (1957) is used. Groups of 5 mice are dosed with the test compound or vehicle control. Sixty minutes later the animals are injected i.p. with 0.3 mL/20 g body weight of a 0.02% solution of phenylbenzoquinone (PBQ; 2-phenyl-1,4-benzoquinone) and placed in individual observation boxes. The number of writhing or abdominal squirming movements made by each mouse during the following 15 minute period is counted. The experiment is repeated with another group of 5 mice and the mean number of writhes per mouse for a group of 10 mice is calculated.

Presentation of Results:

Drug treated and vehicle-treated control groups are compared and the percentage inhibition of writhing conferred by the drug is calculated:

$$\% \text{ inhibition} = \left[ \frac{c-t}{c} \right] \times 100$$

where c=mean number of writhes in the control group, and where t=mean number of writhes in the test drug group.

A still further test used to determine the utility of the compounds of the present invention is designated: PAW PRESSURE TEST IN THE RAT The objective of this test is to assess the potency of peripheral and central acting drugs in inhibiting the reaction of rats to painful stimulation applied to an inflamed paw.

Species:

Male Sprague Dawley rats (180–200 g) are used. The animals are fasted overnight prior to drug administration.

Drug Preparation and Administration:

Freund's Complete Adjuvant (FCA) is prepared by suspending 5 mg killed and dried Mycobacterium butyricum (Difco) in 1 mL liquid paraffin. The test compounds are dissolved or susended in 0.5% Tween 80 in distilled water according to their solubility. They are administered by gastric gavage in a volume of 0.5 mL/100 g body weight to groups of 10 animals.

Methodological Details:

Ten rats are used per group. The method is essentially that described by Randall et al, Arch. Int. Pharmacodyn. III, 409 (1957) and the apparatus which is used to apply pressure to the paw (Analgesy-meter for the rat paw, Ugo Basile from Coulbourn Instruments) is a modification of that described by Gilfoil et al, J. Pharmacol, 142, 1 (1963). The instrument is basically a device which exerts a force that increases at a constant rate. The force is continuously monitored by a pointer moving along a linear scale and is measured in grams. The inflammatory reaction is induced in the left hind paw of rats by injecting 0.1 mL of Freund's adjuvant intradermally. The test compound or vehicle is administered 24 hours after the adjuvant. The pain threshold is determined 1 hour later in the inflamed paw and the normal paw of the treated and control groups.

Presentation of results and Criteria for Activity:

Each animal which has a reading 1.5 times greater than the mean reading of the control-group will be considered as responsive to treatment. The number of animals showing an analgesic effect is then determined in each group.

The $ED_{50}$ (dose which causes analgesia in 50% of the animals) using at least 3 doses is then determined, by the method described in Litchfield et al, J. Pharmacol. Exp. Ther., 96, 99 (1949).

Typical results obtained for the compounds of the prent invention in the aforementioned tests are as follows:

| Preventative Adjuvant Edema | | |
|---|---|---|
| Compound | Dose (mg/kg, p.o.) | % Inhibition |
| Example 1 | 25 | 51 |
| Example 2 | 25 | 36 |

| Phenylquinone Writhing in Mice | | | |
|---|---|---|---|
| Compound | Dose (mg/kg, p.o.) | % Inhibition | $ED_{50}$(mg/kg, p.o.) |
| Example 1 | — | — | 6.6 |
| Example 2 | 25 | 8 | — |

| Paw Pressure Test in Rats | |
|---|---|
| Compound | $ED_{50}$(mg/kg, p.o.) |
| Example 1 | 0.38 |

The lack of side effects for the compounds of this invention are demonstrated by standard acute toxicity tests described by R. A. Turner in "Screening Methods in Pharmacology," Academic Press, New York and London, 1965, pp. 152–163 and by prolonged administration of the compound to warm-blooded animals.

When the compounds of this invention are employed as anti-inflammatory and analgesic agents in warm-blooded animals, they are administered orally, alone or in dosage forms, i.e., capsules or tablets, combined with pharmacologically acceptable excipients, such as starch, milk sugar and so forth, or they are administered orally in the form of solutions in suitable vehicles such as vegetable oils or water. The compounds of this invention may be administered orally in sustained release dosage form or transdermally in ointments or patches. The compounds of this invention may also be administered in the form of suppositories.

The dosage of the compounds of formula I of this invention will vary with the particular compound chosen and form of administration. Furthermore, it will vary with the particular host under treatment. Generally, the compounds of this invention are administered at a concentration level that affords protective effects without any deleterious side effects. These anti-inflammatorily effective concentration levels are usually obtained within a terapeutic range of 1.0 82 g to 500 mg/kg per day, with a preferred range of 10 μg to 100 mg/kg per day.

The compounds of this invention also possess antipyretic activity.

The compounds of this invention may be administered together with the usual doses of caffeine.

The following examples further illustrate this invention.

EXAMPLE 1

1,8-Diethyl-2,3,4,9-tetrahydro-4-(2-propynyl)-1H-carbazole-1-acetic Acid Isomer A Step (1) Preparation of 1-Ethyl-2-hydroxy-3-cyclohexeneethanol A solution of 1-ethyl-2-oxocyclohex-3-eneacetic acid methyl ester (5.00 g, 25.48 mmol) in 10 mL of anhydrous ether was added dropwise under nitrogen to a 0° C. solution of lithium aluminum hydride (967 mg, 25.48 mmol) in 25 mL of anhydrous ether. The reaction was quenched by dropwise addition of 0.97 mL of water, 0.97 mL of 1M NaOH (aqueous) and 2.7 mL of water.

The solution was filtered and the salts were boiled 3× in 25 mL of ethyl acetate and these washings were combined with the first filtrate. The filtrate was concentrated in vacuo to afford 4.47 g (103%) of product as a colorless oil.

NMR (CDCl$_3$/TMS, 200 MHz): δ0.6–0.8 (m, 3H, CH$_3$), 0.9–1.8 (m, 8H, C:CCH$_2$CH$_2$, CH$_2$CH$_2$OH, CH$_2$CH$_3$), 3.1–3.5 (m, 3H, C$\underline{H}_2$OH, C$\underline{HOH}$), 4.6–4.9 (m, 2H, HC:CH)

IR (neat): 3310 (broad OH), 3030 (vinyl CH), 3000–2800 (CH)

Step (2) Preparation of 6-[2-[[(1,1-Dimethylethyl)diphenylsilyl]oxy]ethyl]-6-ethyl-2-cyclohexenol A solution of 1-ethyl-2-hydroxy-3-cyclohexeneethanol (4.3 g, 25.48 mmol) and imidazole (4.44 g, 65.17 mmol) in 31 mL of dry DMF was stirred under nitrogen and treated with tert-butylchlorodiphenylsilane (7.70 g, 7.3 mL, 28.03 mmol). The reaction was poured into 300 mL of 1:1 ether:petroleum ether and washed with 3×100 mL of water. Flash chromatography (75 mm column, 5½ inches of silica gel, 7.5% ethyl acetate/petroleum ether eluent) afforded 8.519 g (82%) of product as a viscous oil.

NMR (CDCl$_3$/TMS, 200 MHz): δ0.722 (t, 3H, J=7.6 Hz, CH$_3$), 1.06 (s, 9H, t-Bu), 1.2–2.1 (m, 8H, C:CCH$_2$CH$_2$, CH$_2$CH$_2$O, CH$_2$CH$_3$), 3.6–4.0 (m, 3H, CH$_2$O, C$\underline{H}$OH), 5.65–5.9 (m, 2H, HC:CH), 7.4–7.9 (m, 10H, aromatics)

IR (neat): 3410 (OH), 3060–3000 (aromatic and vinyl CH)

Step (3) Preparation of 6-[2-[[(1,1-Dimethylethyl)diphenylsilyl]oxy]ethyl]-6-ethyl-2-cyclohexenone Pyridinium dichromate (64.45 g, 171.33 mmol) was added to a solution of 6-[2-[[(1,1-dimethylethyl)diphenylsilyl]oxy]ethyl]-6-ethyl-2-cyclohexenol (56.01 g, 137.06 mmol) in 274 mL of dry N,N-dimethylformamide at 0° C. under nitrogen. After 1 hour, the reaction was poured into 2 L of brine and extracted with 10×500 mL of ether. The ethereal solutions were concentrated in vacuo and flash chromatographed in two batches (95 mm column, 5½ inches of silica gel, 8% ethyl acetate in petroleum ether eluent) to afford 48.94 g (88%) of product as a pale yellow oil.

NMR (CDCl$_3$/TMS, 200 MHz): δ0.76 (t, J=7.6 Hz, 3H, CH$_3$), 1.03 (s, 9H, t-Bu), 1.2–2.3 (m, 8H, C:CCH$_2$CH$_2$, CH$_2$CH$_2$O, CH$_2$CH$_3$), 3.7 (m, 2H, CH$_2$O), 5.86 (d of t, J=10.2, 1.9 Hz, 1H, CHC:O), 6.79 (d of t, 1H, J=9.8, 3.8 Hz, 1H, C:C$\underline{H}$CH$_2$), 7.4–7.9 (m, 10H, aromatics)

IR (neat): 3450 (OH), 3060–3000 (aromatic and vinyl CH), 3000–2800 (CH), 1650 (C:O)

Step (4) Preparation of Tris(1-methylethyl)-1-propynylsilane

1-Propynyllithium (7.18 g, 156 mmol) was stirred in 160 mL of anhydrous ether at −40° C. under nitrogen and treated dropwise with triisopropylsilyl trifluoromethanesulfonate (47.8 g, 41.93 mL, 156 mmol). The reaction was warmed to room temperature, washed with 2×100 mL of water and 1×100 mL of brine. The organic phase was dried over MgSO$_4$ and concentrated in vacuo. Flash chromatography (95 mm column, petroleum ether eluent, 5½ inches of silica gel) afforded 25.7 g (84%) of product as a colorless oil.

NMR (CDCl$_3$/TMS, 60 MHz): δ1.05 (broad s, 21H, iPr), 1.9 (s, 3H, CH$_3$)

IR (neat): 3000–2800 (CH), 2185 (acetylene)

Step (5) Preparation of 2-[2-[[(1,1-Dimethylethyl)diphenylsilyl]oxy]ethyl]-2-ethyl-5-[3-[tris(1-methylethyl)silyl]-2-propynyl]cyclohexanone A stirred solution of tris(1-methylethyl)-1-propynylsilane (9.64 g, 49.18 mmol) in 99 mL of dry tetrahydrofuran under nitrogen was cooled to −20° C. and treated dropwise with n-BuLi (18.92 mL of 2.6M in hexane, 49.18 mmol). After 15 minutes, 33 mL of hexamethylphosphoramide (dried with n-BuLi to a φ$_3$CH endpoint) were added and the reaction was cooled to −78° C. It was treated with a solution of 6-[2-[[(1,1-dimethylethyl)diphenylsilyl]oxy]ethyl]-6-ethyl-2-cyclohexenone (10 g, 24.59 mmol) in 40 mL of dry tetrahydrofuran and quenched 30 minutes later with 100 mL of 1M HCl (aqueous). The reaction was extracted with 4×100 mL of ether and 2×100 mL of petroleum ether. The combined organic layers were concentrated, washed with brine and then stripped of solvent completely. Flash chromatography (95 mm column, 2.5% ethyl acetate/petroleum ether eluent) afforded 8.02 g (54%) of product as a yellow oil.

NMR (CDCl$_3$/TMS, 200 MHz): δ0.66 (broad t, 3H), 0.85 (broad t, 3H), 1.05 (broad s, 27H), 1.2–2.5 (m, 13H), 3.4–3.8 (m, 2H), 7.35–7.7 (m, 10H)

IR (neat): 3060–3000 (aromatic CH), 2160 (acetylene, 1700 (C:O)

Step (6) Preparation of 1-Ethyl-2-oxo-4(2-propynyl)cyclohexaneacetic Acid Methyl Ester 2-[2-[[(1,1-Dimethylethyl)diphenylsilyl]oxy]ethyl]-2-ethyl-5-[3-[tris(1-methylethyl)silyl]-2-propynyl]cyclohexanone (4.29 g, 7.12 mmol) was dissolved in 137 mL of tetrahydrofuran and treated with tetrabutylammonium fluoride (21.36 mL of 1M solution in tetrahydrofuran, 21.36 mmol). After 15 minutes, the reaction was concentrated to about 50 mL and treated with 30 mL of 1M HCl (aqueous) and 30 mL of brine. This mixture was extracted with 5×60 mL of ether and the combined ether layers were dried over MgSO$_4$. Flash chromatography (50 mm column, 15% ethyl acetate in petroleum ether eluent) afforded 984 mg of desilylated material. The R$_f$ of this material was 0.20 in 15% ethyl acetate in petroleum ether on silica gel. A solution of 3.37 g of the R$_f$ 0.20 material in 88 mL of acetone was treated dropwise at 0° C. with 8N Jones reagent (from 106.8 g of CrO$_3$ suspended in 92 mL of concentrated sulfuric acid and diluted to 400 mL with water) until the orange color persisted (∼10.1 mL). Isopropanol was then added to turn the solution green again. The reaction was decanted into 300 mL of ether and the solid residue was washed with an additional 200 mL of ether. The combined ether solutions were washed with a brine/1M HCl mixture at pH=1 (6×100 mL) and back washed with 100 mL ether. The organic phase was dried (MgSO$_4$) and concentrated in vacuo. Flash chromatography (15% ethyl acetate in petroleum ether eluent, 95 mm column) afforded a mixture of diastereomers. The mixture showed up as two spots on a silica gel thin layer chromatography plate. They were separated by reverse phase (C$_{18}$) chromatography to afford a first eluted (isomer A) diastereomer and a second eluted (isomer B) diastereomer. These isomers were treated with ethereal diazomethane to afford the corresponding methyl esters as oils.

Isomer A

NMR (CDCl₃/TMS, 200 MHz): δ0.82 (t, 3H, J=7.5 Hz), 1.3–2.7 (m, 14H), 3.64 (s, 3H)

IR (neat): 3300 (acetylene CH), 3000–2880 (CH), 2100 (acetylene), 1740 (COOMe), 1690 (C=O)

Isomer B

NMR (CDCl₃/TMS, 200 MHz): δ0.79 (t, 3H, J=7.5 Hz), 1.3–2.8 (m, 14H), 3.65 (s, 3H)

IR (neat): 3290 (acetylene CH), 3000–2880 (CH), 2100 (acetylene), 1720 (COOMe), 1690 (C=O)

Step (7) Preparation of 1,8-Diethyl-2,3,4,9-tetrahydro-4-(2-propynyl)-1H-carbazole-1-acetic Acid Methyl Ester A solution of 1-ethyl-2-oxo-4-(2-propynyl)cyclohexaneacetic acid methyl ester isomer B (3.30 g, 13.96 mmol), and 2-ethylphenylhydrazine (2.09 g, 15.36 mmol) was refluxed in 60 mL of methanol under nitrogen for three days. The solution was cooled to 0° C., treated with acetyl chloride (2.19 g, 1.96 mL, 27.92 mmol) and refluxed for 45 minutes under nitrogen. The reaction was then concentrated in vacuo and the product was isolated by flash chromatography (50 mm column, 7% ethyl acetate in petroleum ether eluent) which afforded 1.14 g (24%) of oil which is referred to as 1,8-diethyl-2,3,4,9-tetrahydro-4-(2-propynyl)-1H-carbazole-1-acetic acid methyl ester isomer B.

1-Ethyl-2-oxo-4-(2-propynyl)cyclohexaneacetic acid methyl ester isomer A (1.95 g, 8.33 mmol) was treated in the same manner to afford 452 mg (16%) of 1,8-diethyl-2,3,4,9-tetrahydro-4-(2-propynyl)-1H-carbazole-1-acetic acid methyl ester isomer A as an oil.

Isomer A

NMR (CDCl₃/TMS, 200 MHz): δ0.87 (t, 3H, J=7.5 Hz), 1.38 (t, 3H, J=7.5 Hz), 1.6–3 (m, 11H), 3.2 (m, 1H), 3.72 (s, 3H), 7 (m, 2H), 7.41 (d of d, 1H, J=7.1, 1.8 Hz), 9.5 (broad s, 1H)

IR (CHCl₃): 3400 (NH), 3312 (acetylene CH), 3020–2860 (CH), 2113 (acetylene), 1730 (C=O)

Isomer B

NMR (CDCl₃/TMS, 200 MHz): δ0.85 (t, 3H, J=7.5 Hz), 1.36 (t, 3H, J=7.6 Hz), 1.9–2.4 (m, 8H), 2.60 and 2.74 (2d, ABq, J=16.5 Hz), 2.8 (m, 1H), 2.87 (q, 2H, J=7.6 Hz), 3.2 (m, 1H), 3.67 (s, 3H), 7 (m, 2H), 7.41 (d of d, 1H, J=7.3, 1.3 Hz), 9.1 (broad s, 1H)

IR (CHCl₃): 3450 (NH), 3311 (acetylene CH), 3010–2860 (CH), 2118 (acetylene), 1720 (C=O)

Step (8) Preparation of 1,8-Diethyl-2,3,4,9-tetrahydro-4-(2-propynyl)-1H-carbazole-1-acetic Acid Isomer A A solution of 1,8-diethyl-2,3,4,9-tetrahydro-4-(2-propynyl)-1H-carbazole-1-acetic acid methyl ester isomer A (660 mg, 1.96 mmol) in 8 mL of ethanol and 1.6 mL of 10% NaOH (aqueous) was refluxed for 45 minutes under nitrogen. The ethanol was then removed in vacuo and the residue was dissolved in 5 mL of water. It was acidified to pH 1 with 1M HCl (aqueous) and extracted with 4×20 mL of ether. Drying (MgSO₄) and flash chromatography (40 mm column, 2% H₃PO₄ in methanol treated silica gel, 10% ethyl acetate in petroleum ether eluent) afforded 630 mg (100%) of oil. The product was crystallized from 85:15 petroleum ether/benzene giving 538 mg of off-white crystals, m.p. b 139°–141° C.

NMR (CDCl₃/TMS, 200 MHz): δ0.90 (t, 3H, J=7.5 Hz), 1.34 (t, 3H, J=7.6 Hz), 1.8–2.5 (m, 8H), 2.76 (m, 2H), b 2.83 (q, 2H, J=7.6 Hz), 2.9 (m, 1H), 3.3 (m, 1H), 7 (m, 2H), 7.42 (d, 1H, J=7.6 Hz), 9.08 (broad s, 1H)

IR (KBr): 3400 (NH), 3300 (acetylene CH), 3050–2860 (CH), 2110 (acetylene), 1690 (C=O)

Anal. Calcd.: C, 77.99; H, 7.79; N, 4.33%. Found: C, 77.71; H, 7.72; N, 4.20%

EXAMPLE 2

1,8-Diethyl-2,3,4,9-tetrahydro-4-(2-propynyl)-1H-carbazole-1-acetic Acid Isomer B A solution of 1,8-diethyl-2,3,4,9-tetrahydro-4-(2-propynyl)-1H-carbazole-1-acetic acid methyl ester isomer B (106 g, 3.14 mmol) in 9 mL of ethanol and 2.6 mL of 10% NaOH (aqueous) was refluxed for 1.5 hours under nitrogen. The ethanol was removed in vacuo and the residue was dissolved in water and acidified to pH 1 with 1M HCl (aqueous). It was extracted with 4×30 mL of ether, dried over magnesium sulfate and concentrated in vacuo. Flash chromatography (40 mm column, 2% H₃PO₄ in methanol treated silica gel, 12% ethyl acetate in petroleum ether eluent) afforded 958 mg (97%) of oil which was crystallized from 85:15 petroleum ether/benzene to give 826 mg of product as pale yellow crystals, m.p. 146°–148° C.

NMR (CDCl₃/TMS, 200 MHz): δ0.87 (t, 3H, J=7.5 Hz), 1.33 (t, 3H, J=7.6 Hz), 1.6 (m, 1H), 2–2.4 (m, 6H), 2.4 (broad m, 1H), 2.8 (broad m, 5H), 3.2 (m, 1H), 7 (m, 2H), 7.41 (d, 1H, J=7.3 Hz), 8.81 (broad s, 1H)

IR (KBr): 3460 (NH), 3300 (acetylene CH), 3060–2880 (CH), 2100 (acetylene), 1700 (C=O)

Anal. Calcd.: C, 77.99; H, 7.79; N, 4.33%. Found: C, 78.06; H, 7.85; N, 4.23%

We claim:

1. A compound of the formula (I)

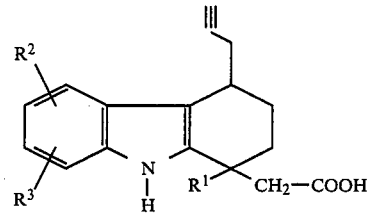

wherein R¹ is hydrogen or lower alkyl containing 1 to 6 carbon atoms; R² and R³ are independently hydrogen, halogen or lower alkyl containing 1 to 6 carbon atoms and the pharmaceutically acceptable salts thereof.

2. A compound of the formula (II)

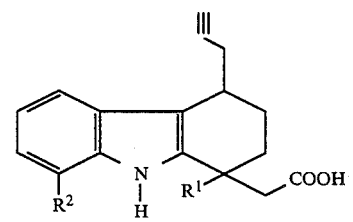

wherein R¹ is hydrogen or lower alkyl containing 1 to 6 carbon atoms; and R² is hydrogen, halogen or lower alkyl containing 1 to 6 carbon atoms and the pharmaceutically acceptable salts thereof.

3. A compound according to claim 2 wherein $R^1$ and $R^2$ are lower alkyl containing 1 to 6 carbon atoms and the pharmaceutically acceptable salts thereof.

4. A compound according to claim 4 designated 1,8-diethyl-2,3,4,9-tetrahydro-4-(2-propynyl)-1H-carbazole-1-acetic acid and the pharmaceutically acceptable salts thereof.

5. A pharmaceutical composition comprising a compound of structure (I), or a pharmaceutically acceptable salt thereof, as defined in claim 1 and a pharmaceutically acceptable carrier.

6. A method for treating inflammatory or painful conditions in a mammal which comprises the administration to said mammal of an effective amount of a compound selected from those of formula (I), or a pharmaceutically acceptable salt thereof, as defined in claim 1.

7. A compound of formula (XII)

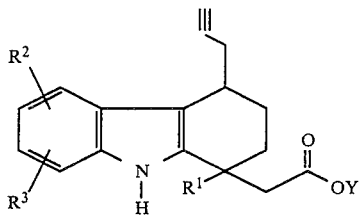

(XII)

wherein $R^1$ is hydrogen or lower alkyl containing 1 to 6 carbon atoms; $R^2$ and $R^3$ are independently hydrogen, halogen or lower alkyl containing 1 to 6 carbon atoms; and Y is lower alkyl containing 1 to 6 carbon atoms.

* * * * *